US005738858A

United States Patent [19]
Burger

[11] Patent Number: 5,738,858
[45] Date of Patent: Apr. 14, 1998

[54] SKIN CARE COMPOSITIONS CONTAINING FATTY HYDROXYETHYL IMIDAZOLINE SURFACTANTS AND RETINOL OR RETINYL ESTER

[75] Inventor: Allan Robert Burger, Passaic, N.J.

[73] Assignee: Cheseborough-Pond's USA Co., Division of Conopco, Inc., Greenwich, Conn.

[21] Appl. No.: 721,875

[22] Filed: Sep. 27, 1996

[51] Int. Cl.$^6$ ..................................................... A61K 7/48
[52] U.S. Cl. .......................... 424/401; 424/59; 514/725; 514/844; 514/846; 514/937

[58] Field of Search ........................... 424/401, 70.31, 424/59; 514/844, 846, 937, 725

[56] References Cited

U.S. PATENT DOCUMENTS 5,536,740  7/1996  Granger et al. .................... 514/392

*Primary Examiner*—Jyothsan Venkat
*Attorney, Agent, or Firm*—Rimma Mitelman

[57] ABSTRACT

Fatty hydroxyethyl imidazolines inhibit esterification of retinol into inactive retinyl esters. Thus, effects of the retinol or retinyl esters in combination with fatty hydroxyethyl imidazolines are analogous to treatment with retinoic acid.

3 Claims, No Drawings

SKIN CARE COMPOSITIONS CONTAINING FATTY HYDROXYETHYL IMIDAZOLINE SURFACTANTS AND RETINOL OR RETINYL ESTER

FIELD OF THE INVENTION

The present invention relates to skin care compositions containing fatty hydroxyethyl imidazoline surfactants and retinol or retinyl ester.

BACKGROUND OF THE INVENTION

Retinol (vitamin A) is an endogenous compound which occurs naturally in the human body and is essential for normal epithelial cell differentiation. Natural and synthetic vitamin A derivatives have been used extensively in the treatment of a variety of skin disorders and have been used as skin repair or renewal agents. Retinoic acid has been employed to treat a variety of skin conditions, e.g., ache, wrinkles, psoriasis, age spots and discoloration. See e.g., Vahlquist, A. et al., *J. Invest. Dermatol.*, Vol. 94, Holland D. B. and Cunliffe, W. J. (1990), pp. 496–498; Ellis, C. N. et al., "Pharmacology of Retinols in Skin", Vasel, Karger, Vol. 3, (1989), pp. 249–252; Lowe, N.J. et al., "Pharmacology of Retinols in Skin", Vol. 3, (1989), pp. 240–248; PCT Patent Application No. WO 93/19743.

It is believed that the use of retinol or esters of retinol would be preferred over retinoic acid. Retinol is an endogenous compound which occurs naturally in the human body and is essential for normal epithelial cell differentiation. Retinol is also considered much safer than retinoic acid. Esters of retinol hydrolyze in-vivo to produce retinol. It is believed that retinyl esters and retinol are metabolically converted in the skin into retinoic acid according to the following mechanism:

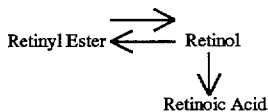

However, most of the endogenously applied retinol is rapidly converted into inactive retinyl esters for storage in epidermal cells (keratinocytes). Esterification of retinol into inactive retinyl esters is achieved in cells by transfer of a fatty acyl group from an acyl CoA, catalyzed by the enzyme acyl CoA retinol transferase (ARAT), or by the transfer of an acyl group from phosphatidyl choline, catalyzed by the enzyme lecithin retinol acyl transferase (LRAT). These esterification reactions are very efficient in keratinocytes—the majority (95%) of cellular retinoids are in the form of retinyl fatty esters. Thus, unfortunately, although retinol and retinyl esters are safer to use than retinoic acid, they are less effective than retinoic acid at providing skin benefits.

The present invention is based, in part, on the discovery that certain compounds, i.e. fatty hydroxyethyl imidazoline suffactants, inhibit these esterification reactions and thus potentiate the action of retinol by increasing the amount of retinol available for conversion to retinoic acid. Thus, a mixture of fatty hydroxyethyl imidazolines with retinol or retinyl esters mimics retinoic acid yet is safer to use than retinoic acid.

SUMMARY OF THE INVENTION

The present invention includes, in part, a skin conditioning composition containing:

(a) from about 0.001% to about 10% of retinol or a retinyl ester;

(b) from about 0.0001% to about 50% of a fatty hydroxyethyl imidazoline; and (c) a cosmetically acceptable vehicle.

The term "conditioning" as used herein means prevention and treatment of dry skin, photodamaged skin, appearance of wrinkles, age spots, aged skin, increasing stratum corneum flexibility, lightening skin color, controlling sebum excretion and generally increasing the quality of skin. The composition may be used to improve skin desquamation and epidermal differentiation.

The presence of the fatty hydroxyethyl imidazoline in the inventive product substantially improves the performance of retinol or a retinyl ester.

In a preferred embodiment of the invention, retinol or a retinyl ester is used in conjunction with $C_8$–$C_{18}$ hydroxyethyl imidazoline, most preferably oleyl ($C_{18}$) hydroxyethyl imidazoline.

According to the present invention, by virtue of including an effective amount of a fatty hydroxyethyl imidazoline into compositions containing retinol or a retinyl ester, the performance of the compositions is substantially improved. Alternatively, lower levels of retinol or a retinyl ester may be included in the composition containing the fatty hydroxyethyl imidazoline to equal the performance of a similar formulation without the imidazoline.

DESCRIPTION OF THE PREFERRED EMBODIMENT

The inventive compositions contain, as a first essential ingredient, a compound selected from the group consisting of retinol or a retinyl ester. The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate.

The preferred ester for use in the present invention is selected from retinyl palmitate, retinyl acetate and retinyl propionate, because these are the most commercially available and therefore the cheapest. Retinyl linoleate ester is also preferred due to its efficacy.

Retinol or retinyl ester is employed in the inventive composition in an amount of from about 0.001% to about 10%, preferably in an amount of from about 0.01% to about 1%, most preferably in an amount of from about 0.01% to about 0.5%.

The second essential ingredient of the inventive compositions is a fatty hydroxyethyl imidazoline, which has the following general structure:

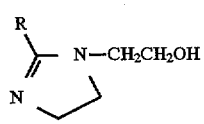

wherein R is an aliphatic saturated or unsaturated, straight or branched hydrocarbon chain containing from 8 to 20 carbon atoms.

Examples of suitable fatty hydroxyethyl imidazolines include but are not limited to cocoylhydroxyethyl imidazoline (R is derived from coconut oil fatty acids, mostly $C_{12}$ and some longer chain), lauryl hydroxyethyl imidazoline ($R=CH_3(CH_2)_{10}$, myristyl hydroxyethyl imidazoline ($R=CH_3(CH_2)_{12}$), stearyl hydroxyethyl imidazoline ($R=CH_3(CH_2)_{6}$ and oleyl hydroxyethyl imidazoline ($R=CH_3(CH_2)_7CH=CH(CH_2)_7$)

Preferably, R in the fatty hydroxyethyl imidazoline contains from 8 to 18 carbon atoms, most preferably from 11 to 18 carbon atoms.

Most preferably, the fatty hydroxyethyl imidazoline is oleyl hydroxyethyl imidazoline, due to its commercial availability and efficacy.

The fatty hydroxyethyl imidazoline is included in the inventive compositions in an amount ranging from about 0.0001% to about 50%, preferably from about 0.01% to about 10%, most preferably from about 0.1% to about 5%.

Cosmetically Acceptable Vehicle

The composition according to the invention also comprises a cosmetically acceptable vehicle to act as a dilutant, dispersant or carrier for the active components in the composition, so as to facilitate their distribution when the composition is applied to the skin.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively.

The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic acid, columbinic acid, eicosa-(n-6,9,13)-trienoic acid, arachidonic acid, γ-linolenic acid, timnodonic acid, hexaenoic acid and mixtures thereof.

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate(a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled or aged skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion, a fluid cream, a cream or a gel. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-odeformable bottle or squeeze container, such as a tube or a lidded jar.

The invention accordingly also provides a closed container containing a cosmetically acceptable composition as herein defined.

The following specific examples further illustrate the invention, but the invention is not limited thereto.

MATERIALS AND METHODS

Cell Culture

Human keratinocytes, isolated from neonatal foreskin by trypsin treatment were grown in Dulbecco Modification Eagle (DME) Hams F12 (1:1) medium/10% fetal calf serum in the presence of irradiated 3T3 mouse fibroblasts for establishing dividing keratinocyte colonies. Cells were grown under the above condition until their second passage and kept frozen for future use. Frozen second passage keratinocytes were thawed and plated into the above medium and grown for five days before they were switched to a serum-free MCDB 153-based medium keratinocyte growth medium (KGM) from Clonetics Corporation, San Diego, Calif., containing 0.15 mM Ca, or keratinocyte serum-free media (KSFM) from GIBCO containing 0.09 mM Ca). On day 7, when the cells were 80–90% confluent, they were trypsinized and plated in the serum-free medium for the various experiments.

Thymidine Assay $^3$H-Thymidine Incorporation and Keratinocyte Proliferation

The incorporation of $^3$ H-thymidine by cultured keratinocytes was used as an assay of keratinocyte proliferation. Thymidine is one of four deoxynucleosides which are the monomeric units of DNA, the universal library of genetic information in the animal kingdom. Prior to cell division of a somatic cell such as a keratinocyte, the complete genome of the cell undergoing cell division is replicated. This involves large scale DNA synthesis by the cell and enables both daughter cells to receive identical copies of the genetic material. When $^3$H-thymidine is included in the culture media of keratinocytes which are synthesizing DNA in preparation for cell division then the labelled nucleoside is incorporated into the newly synthesized DNA. The extent of incorporation of $^3$ H-thymidine into a population of cells is proportional to the rate of DNA synthesis by this population of cells and therefore an indication of their cellular proliferation.

Keratinocytes (that were cultured as described above) were plated in 24 well plates at a density of 20,000 cells per well in 1 ml media. After incubation for four days or until the cells were 60–70% confluent, the media was changed. Test compounds were added (in triplicate) to the wells 24 hours after the media change, and four hours later 1 µCi $^3$H-Thymidine in 50 µl media was added per well. Cells were incubated for a further 24 hours. Media was removed from the cells, 10% ice cold trichloroacetic acid (TCA) added and plates were incubated on ice for 30 minutes. Cells were washed five times with 5% TCA and allowed to dissolve in 500 µl 0.1M NaOH for at least one hour (usually overnight). The preparations were neutralized with 0.1M HCl; 50 µl of the cell preparation was used to determine total protein content. Disintegrations per minute (DPM) from $^3$H labelling of DNA was determined by liquid scintillation counting of 9001 µl of the cell preparation. Thymidine incorporation results were expressed as DPM/µg protein.

Transglutaminase Assay

Transglutaminase Assay and Keratinocyte Differentiation

During the process of terminal differentiation in the epidermis, a 15 nm thick layer of protein, known as the cornified envelope (CE) is formed on the inner surface of the cell periphery. The CE is composed of numerous distinct proteins which have been cross-linked together by the formation of N $^\epsilon$-(γ-glutamyl) lysine isodipeptide bonds catalyzed by the action of at least two different transglutaminases (TGases) expressed in the epidermis. TGase 1 is expressed in abundance in the differentiated layers of the epidermis, especially the granular layer, but is absent in the undifferentiated basal epidermis. Thus TGase 1 is a useful marker of epidermal keratinocyte differentiation with high TGase 1 levels indicating a more differentiated state. An ELISA based TGase 1 assay, using a TGase 1 antibody, was used to assess the state of differentiation of the cultured keratinocytes in the examples that follow.

For Example 1, the following procedure was used:

Keratinocytes (cultured as described above) were plated in 96 well plates at a density of 3,000 cells per well in 200 µl media. After incubation for four days the media was changed to media containing test compounds (six replicates per test). The cells were cultured for a further 72 hours after which time the media was aspirated and the plates stored at −70° C. Plates were removed from the freezer, and the cells washed with PBS. 100 µl sterile water was added and the cells were freeze fractured by freezing at −70° C. then thawing. The cells were incubated for one hour at room temperature (R/T) with PBS/3% BSA (wash buffer, bovine serum albumin), then rinsed with a fresh aliquot of wash buffer. Cells were incubated with 50 µl of primary antibodies monoclonal anti-human transglutaminase mouse antibody (IgG) obtained from Biomedical Industries diluted 1:2,000 in wash buffer for one hour, 37° C. then rinsed two times with wash buffer. Cells were then incubated with 50 µl of secondary antibody (Fab fragment, peroxidase conjugated anti-mouse IgG obtaining from Amersham) diluted 1:4,000 in wash buffer for one hour at 37° C., then rinsed two times with wash buffer. Cells were incubated with substrate solution (4 mg o-phenylene diamine and 3.3 µl 30% $H_2O_2$ in 10 ml 0.1M citrate buffer pH 5.0) for five minutes, R/T, in darkness (under aluminum foil). The reaction was stopped by the addition of 50 µl 4N $H_2SO_4$. The absorbance of samples was read at 492 nm in the plate reader. Out of the six replicates, four were treated with both antibodies, two were treated only with the secondary antibody (i.e., to determine background binding of enzyme conjugated Ab). TGase levels were determined by subtracting background from the readings from each treatment and determining mean±s.d. for the replicates exposed to both Ab.

For Example 4, the following procedure was used:
Keratinocytes (cultured as described above) were plated in 96 well plates at a density of 3,000 cells per well in 2000 µl of cell culture media. After incubation for four days, the media was changed to media containing test compounds (six replicates per test). The cells were cultured for a further 72 hours after which time the media was aspirated and the plates stored at −70° C. After the plates were removed from the freezer, the cells were further freeze fractured by freezing and thawing and then washed 3× with PBS. The cells were incubated for one hour at room temperature (R/T) with TBS/5% BSA buffer. Cells were then incubated with 100 µl of monoclonal anti-human transglutaminase (IgG) mouse antibody (primary antibody) obtained from Biomedical Technologies Inc. diluted 1:2000 in TBS/1% BSA buffer for two hours at 37° C., and then rinsed six times with wash buffer (TBS/1% BSA/0.05% Tween-20). Cells were next incubated with 100 µl of Fab fragment, peroxidase conjugated anti-mouse IgG antibody (secondary antibody) from Amersham diluted 1:4,000 in wash buffer for two hours at 37° C. and then rinsed three times with wash buffer and three times with PBS. Cells were incubated with substrate solution (4 mg o-phenylene diamine and 3.3 µl 30% $H_2O_2$ in 10 mL 0.1M citrate buffer, pH 5.0) for five minutes at R/T and in darkness (under aluminum foil). The reaction was stopped by the addition of 50 µl 4N $H_2SO_4$. The absorbance of samples was read at 492 nm in the plate reader. Out of the six replicates, four were treated with both antibodies, two were treated only with the secondary antibody (i.e., to determine the background binding of the enzyme conjugated antibody). Transglutaminase I levels were determined by subtracted background from the readings from each treatment and determining the mean s.d. for the replicates exposed to both antibodies.

DNA Assay

The level of TGase-1 detected after treatment of the cells could be influenced by cell number, i.e., the greater the number of cells the greater the level of TGase-1 detected. The level of TGase-1 was normalized to DNA content of the cells in the same well thus eliminating variation due to differences in cell number. DNA quantitation is a particularly useful indicator of cell number, including keratinocyte cell number, because each cell has to all intents and purposes an identical genome and therefore an identical quantity of DNA. The total DNA content of a well of cells therefore is directly proportional to the cell number in that well. Quantitation of DNA was used to normalize the TGase data to cell number.

Keratinocytes were plated in 96 well plates at a density of 3,000 cells per well in 200 µl media. After incubation for four days the media was changed for media containing test compounds (6 replicates per test). The cells were cultured for a further 72 hours after which time the media was aspirated and the plates stored for at least 1.5 hours at −70° C. Plates were removed from the freezer and thawed for 30 minutes. 100 µl/well of Hoechst dye (1 µl/ml final concentration) was added and this was incubated for 15 minutes, covered and then read in a fluorimeter (ex. 360 nm and em. 460 nm). The dye solution was removed and the wells were rinsed with PBS in preparation for the TGase assay.

EXAMPLE 1

Retinoic Acid is More Effective than Retinol at Altering Keratinocyte Differentiation State A. The effect on incorporation of $^3$H-thymidine µg soluble protein 24 hours after the addition of retinoic acid or retinol at various concentrations was examined. The results that were obtained are summarized in Table 1A.

TABLE 1A

Effect of Retinoic Acid (RA) and Retinol (ROH) on Keratinocyte Thymidine Incorporation

| Treatment | mean Thymidine incorp./µg protein ± s.d (% control) | p value vs Control | p value vs $10^{-7}$M ROH | p value vs $10^{-8}$M ROH | p value vs $10^{-9}$M ROH |
| --- | --- | --- | --- | --- | --- |
| Control | 2094 ± 140 (100%) | — | 0.202 | 0.501 | 0.203 |
| 2.5 × $10^{-7}$M RA | 2475 ± 116 (118%) | 0.005 | 0.032 | 0.004 | 0.002 |
| 2.5 × $10^{-7}$M ROH | 2218 ± 73 (106%) | 0.202 | — | 0.021 | 0.005 |
| 2.5 × $10^{-8}$M RA | 2686 ± 72 (128%) | 0.001 | 0.001 | 0.001 | 0.001 |
| 2.5 × $10^{-8}$M ROH | 2034 ± 46 (97%) | 0.501 | 0.021 | — | 0.121 |
| 2.5 × $10^{-9}$M RA | 2556 ± 80 (122%) | 0.001 | 0.006 | 0.001 | 0.001 |
| 2.5 × $10^{-9}$M ROH | 1977 ± 19 (94%) | 0.203 | 0.005 | 0.121 | — | n = 3

All concentrations of retinoic acid tested, i.e., 2.5×$10^{-7}$M, 2.5×$10^{-8}$ and 2.5×$10^{-9}$M, significantly increased keratinocyte proliferation over both the ethanol control and each of the 2.5×$10^{-7}$M, 2.5×$10^{-8}$M and 2.5×$10^{-9}$M retinol treatments and they did so in a dose dependant manner. This is consistent with retinoic acid having a greater stimulatory effect on epithelial proliferation than retinol.

B. The effect on Transglutaminase levels normalized to DNA content of the cells after addition of retinoic acid and retinol was examined and the results are shown in Table 1B.

TABLE 1B

| Treatment | mean TGase/ DNA × $10^{-4}$ ± s.d (% control) | p value vs Control | p value vs $10^{-7}$ROH | p value vs $10^{-8}$ROH | p value vs $10^{-9}$ROH |
|---|---|---|---|---|---|
| Control | 2.44 ± 0.24 (100%) | — | 0.001 | 0.001 | 0.001 |
| 2.5 × $10^{-7}$M RA | 0.16 ± 0.11 (7%) | 0.001 | 0.001 | 0.001 | 0.001 |
| 2.5 × $10^{-7}$M ROH | 1.14 ± 0.22 (47%) | 0.001 | — | 0.001 | 0.001 |
| 2.5 × $10^{-8}$M RA | 1.34 ± 0.40 (55%) | 0.001 | 0.001 | 0.001 | 0.001 |
| 2.5 × $10^{-8}$M ROH | 1.89 ± 0.30 (77%) | 0.001 | 0.001 | — | 0.001 |
| 2.5 × $10^{-9}$M RA | 1.87 ± 0.49 (77%) | 0.001 | 0.001 | 0.784 | 0.001 |
| 2.5 × $10^{-9}$M ROH | 2.70 ± 0.59 (>100%) | 0.001 | 0.001 | 0.001 | — | n = 3

All concentrations of retinoic acid tested, i.e., $2.5\times10^{-7}$M, $2.5\times10^{-8}$M and $2.5\times10^{-9}$M decreased keratinocyte differentiation over both the ethanol control and did so to a significantly greater extent than each of the corresponding $2.5\times10^{31\ 7}$M, $2.5\times10^{-8}$M and $2.5\times10^{-9}$M retinol treatments. The decrease in transglutaminase level was dose dependent for both retinoic acid and retinol. This is consistent with retinoic acid having a greater inhibitory effect on epithelial differentiation than retinol.

EXAMPLE 2

Method of in Vitro Microsomal Esterification of Retinol

Microsomes are obtained as described in: J. C. Saari and D. L. Bredberg, "CoA and Non-CoA Dependent Retinol Esterification in Retinal Pigment Epithelium" J. Biol. Chem. 23, 8084–90 (1988).

A solution containing 0.1M sodium phosphate pH 7 buffer, 5 mM dithiothreitol, 2 mg/ml bovine serum albumin, 40 micromolar palmitoyl CoA, 40 micromolar dilauroyl phosphatidyl choline, 10 micromolar retinol and a test compound or solvent blank, was incubated for 1 hour at 37° C. with a microsomal fraction isolated from bovine retinal pigment epithelial cells. After incubation, the reaction was quenched by addition of an equal volume of ethanol, and the retinyl esters formed (retinyl palmitate from the ARAT catalyzed reaction, and retinyl laurate from the LRAT catalyzed reaction) were extracted with hexane. The hexane layer was removed, evaporated under nitrogen, and the residue analyzed by HPLC on a 3.9×300 mm C18 reversed phase column using a 80% methanol in tetrahydrofuran mobile phase and fluorescence detection (325 nm excitation, 480 nm emission) to quantitate the retinyl esters. The quantity of ester formed in the presence of the solvent blank was taken as 100%, and this was used to calculate the percent inhibition of ester formation for the compounds tested. As a control, an aliquot of microsomes was inactivated by boiling for 5 minutes, which resulted in at least 95% inhibition of ester formation.

The results that were obtained are summarized in Table 2.

TABLE 2

| COMPOUND | CONCENTRATION (µM) | % INHIB. ARAT | % INHIB. LRAT |
|---|---|---|---|
| oleyl hydroxyethyl imidazoline | 100 | 90 | 95 |
| oleyl hydroxyethyl imidazoline | 10 | 14 | 28 |
| caprylic hydroxyethyl imidazoline | 100 | — | 8 |
| diazolidinyl urea | 0 | 0 | 0 |
| thiamine | 100 | 0 | 0 |
| caffeine | 100 | 0 | 0 |
| adenine | 100 | 0 | 0 |
| phenyl benzimidazole sulfonic acid | 100 | 0 | 0 |
| uracil | 100 | 0 | 0 |
| tryptophan | 100 | 0 | 0 |
| cocoglutamate | 100 | 0 | 0 |
| dimethyl cocamine oxide | 100 | 0 | 0 |
| disodium cocamphodiacetate | 100 | 0 | 0 |
| oleamidopropyl betaine | 100 | 0 | 0 |
| oleamine oxide | 100 | 0 | 0 |
| lauroyl sarcosine | 100 | 20 | 0 |

It can be seen that the oleyl hydroxyethyl imidazoline surfactant is a potent esterification inhibitor, while other surfactants and other heterocyclic compounds were essentially inactive. Caprylic hydroxyethyl imidazoline (R=$CH_3$ $(CH_2)_6$) did not sufficiently inhibit LRAT.

EXAMPLE 3

Example 2 was repeated with various hydroxyethyl imidazoline surfactants, having R groups as indicated in Table 3. The results that were obtained are summarized in Table 3.

TABLE 3

| R GROUP | CONCENTRATION (MICROMOLAR) | % INHIB. ARAT | % INHIB. LRAT |
|---|---|---|---|
| Oleyl | 100 | 90 | 90 |
| Oleyl | 10 | 15 | 12 |
| Lauryl | 100 | 53 | 47 |
| Lauryl | 10 | 0 | 0 |
| Coco | 100 | 68 | 65 |
| Coco | 10 | 0 | 0 |

The results in Table 3 show relative activity oleyl>coco>lauryl. Coco is better probably because it is not purely $C_{12}$, but has some longer chain alkyl groups as well.

The data in Table 2 on caprylic hydroxyethyl imidazoline showed only 8% inhibition at 100 micromolar. Taken together the data clearly shows relative activity oleyl>coco>lauryl>>caprylic.

EXAMPLE 4

Transglutaminase Assay was conducted using oleyl hydroxyethyl imidazoline (OHI), retinoic acid (RA), retinol (ROH), and retinyl palmitate (RP).

The results that were obtained are summarized in Table 4.

TABLE 4

| Exp# | Compound(s) | Concentration (Micromolar) | % of Control |
| --- | --- | --- | --- |
| 1 | RA | 0.25 | 35.1 |
| 1 | ROH | 0.25 | 76.2 |
| 1 | OHI | 1 | 80.7 |
| 1 | ROH + OHI | 0.25 + 1 | 45.1 |
| 2 | RA | 0.25 | 43.4 |
| 2 | ROH | 0.025 | 91.6 |
| 2 | OHI | 1 | 78.2 |
| 2 | ROH + OHI | 0.025 + 1 | 57.9 |
| 3 | RA | 0.25 | 45.9 |
| 3 | RP | 0.25 | 91.6 |
| 3 | OHI | 1 | 91.1 |
| 3 | RP + OHI | 0.25 + 1 | 71.6 |

It can be seen from the results in Table 4 that retinoic acid substantially decreased keratinocyte differentiation whereas retinol, oleyl hydroxyethyl imidazoline, and retinyl palmitate did not affect keratinocyte differentiation when used alone.

In experiments 1 and 2, when retinol was combined with oleyl hydroxyethyl imidazoline, the result was a synergistic decrease in keratinocyte differentiation, to levels approaching the effect of retinoic acid.

In experiment 3, when oleyl hydroxyethyl imidazoline was combined with retinyl palmirate, the result was not as dramatic as in experiments 1 and 2, but nevertheless a synergistic decrease was observed.

EXAMPLE 5

This example illustrates a high internal phase water-in-oil emulsion incorporating the inventive composition.

| | % w/w |
| --- | --- |
| Retinol | 0.5 |
| Fully hydrogenated coconut oil | 3.9 |
| oleyl hydroxyethyl imidazoline | 5 |
| Brij 92* | 5 |
| Bentone 38 | 0.5 |
| MgSO$_4$7H$_2$O | 0.3 |
| Butylated hydroxy toluene | 0.01 |
| Perfume | qs |
| Water | to 100 |

*Brij 92 is polyoxyethylene (2) oleyl ether

EXAMPLE 6

This example illustrates an oil-in-water cream incorporating the inventive composition.

| | % w/w |
| --- | --- |
| Retinol | 0.15 |
| Mineral oil | 4 |
| Oleyl hydroxyethyl imidazoline | 1 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 7

This example illustrates an alcoholic lotion incorporating the composition according to the invention.

| | % w/w |
| --- | --- |
| Retinyl palmitate | 0.15 |
| Oleyl hydroxyethylimidazoline | 0.1 |
| Ethanol | 40 |
| Perfume | qs |
| Butylated hydroxy toluene | 0.01 |
| Water | to 100 |

EXAMPLE 8

This example illustrates another alcoholic lotion containing the inventive composition.

| | % w/w |
| --- | --- |
| Retinol | 0.15 |
| Cocoylhydroxyethyl imidazoline | 0.1 |
| Ethanol | 40 |
| Antioxidant | 0.1 |
| Perfume | qs |
| Water | to 100 |

EXAMPLE 9

This example illustrates a suncare cream incorporating the composition of the invention:

| | % w/w |
| --- | --- |
| Retinol | 0.01 |
| Oleyl hydroxyethylimidazoline | 0.1 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 10

This example illustrates a non-aqueous skin care composition incorporating the inventive combination.

|  | % w/w |
|---|---|
| Retinyl palmitate | 0.15 |
| Oleyl hydroxyethylimidazoline | 1 |
| Silicone gum SE-30[1] | 10 |
| Silicone fluid 345[2] | 20 |
| Silicone fluid 344[3] | 55.79 |
| Squalene | 10 |
| Linoleic acid | 0.01 |
| Cholesterol | 0.03 |
| 2-hydroxy-n-octanoic acid | 0.7 |
| Vitamin E linoleate | 0.5 |
| Herbal oil | 0.5 |
| Ethanol | 2 |

[1] A dimethyl silicone polymer having a molecular weight of at least 50,000 and a viscosity of at least 10,000 centistokes at 25° C., available from GEC
[2] Dimethyl siloxane cyclic pentamer, available from Dow Corning Corp.
[3] Dimethyl siloxane tetramer, available from Dow Corning Corp.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin conditioning composition comprising
(a) from about 0.001% to about 10% of a compound selected from the group consisting of retinol and (a) retinyl palmitate;
(b) from about 0.0001% to about 50% of a fatty hydroxyethyl imidazoline surfactant having the following structure:

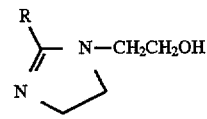

wherein R is an aliphatic saturated or unsaturated, straight or branched hydro-carbon chain containing from 11 to 18 carbon atoms; and
(c) a cosmetically acceptable vehicle.

2. The composition of claim 1 wherein the composition comprises retinol and oleyl hydroxyethyl imidazoline.

3. A method of treating a skin condition selected from the group consisting of dry skin, photodamaged skin, wrinkles, age spots, acne, skin lightening, psoriasis and atopic dermatosis, the method comprising applying to the skin the composition of claim 1.

* * * * *